United States Patent [19]

Uflacker

[11] Patent Number: 5,443,078
[45] Date of Patent: Aug. 22, 1995

[54] METHOD FOR ADVANCING A GUIDE WIRE

[75] Inventor: Renan Uflacker, San Paulo, Brazil

[73] Assignee: InterVentional Technologies, Inc., San Diego, Calif.

[21] Appl. No.: 268,769

[22] Filed: Jun. 29, 1994

Related U.S. Application Data

[63] Continuation-in-part of Ser. No. 120,473, Sep. 13, 1993, abandoned, which is a continuation of Ser. No. 944,473, Sep. 14, 1992, Pat. No. 5,243,997.

[51] Int. Cl.⁶ .............................................. A61B 5/00
[52] U.S. Cl. ................................................... 128/772
[58] Field of Search ....................... 128/657, 658, 772; 604/95, 280–283

[56] References Cited

U.S. PATENT DOCUMENTS

| | | |
|---|---|---|
| 3,315,663 | 11/1967 | Goldfarb . |
| 3,589,363 | 6/1971 | Banko et al. . |
| 3,823,717 | 7/1974 | Pohlman et al. . |
| 3,900,023 | 8/1975 | McBride . |
| 4,504,264 | 3/1985 | Kelman . |
| 4,686,982 | 8/1987 | Nash . |
| 4,696,667 | 9/1987 | Masch . |
| 4,800,890 | 1/1989 | Cramer . |
| 4,844,092 | 7/1989 | Rydell et al. . |
| 4,854,325 | 8/1989 | Stevens . |
| 4,861,332 | 8/1989 | Parisi . |
| 4,898,575 | 2/1990 | Fischell et al. . |
| 4,957,117 | 9/1990 | Wysham . |
| 5,026,384 | 6/1991 | Farr et al. . |
| 5,161,534 | 11/1992 | Berthiaume .................. 128/657 |

Primary Examiner—Max Hindenburg
Attorney, Agent, or Firm—Nydegger & Associates

[57] ABSTRACT

A method of using a hand held vibrating device for transversely vibrating a guide wire in performing angioplasty and atherectomy procedures. The sinusoidal vibrations introduced into the wire by the vibrating device permit the guide wire to be more easily passed through a blood vessel or a stenotic segment of a blood vessel. The guide wire is threaded through a blood vessel until resistance is met. The guide wire can then be clamped to the vibrating device, which is selectively actuated and manipulated to sinusoidally vibrate the wire, overcoming the resistance, and facilitating the further advancement of the guide wire.

12 Claims, 4 Drawing Sheets

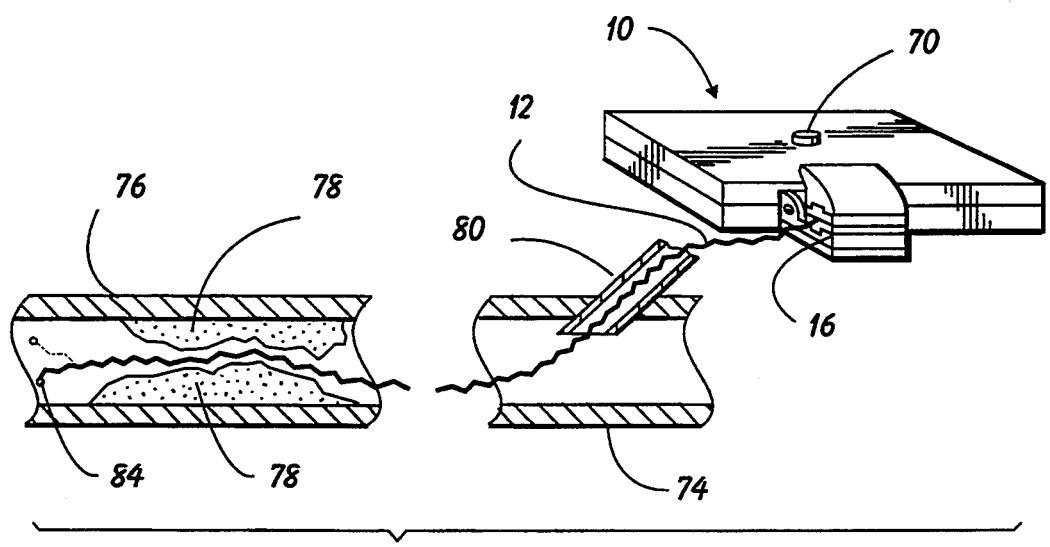
FIGURE 4.
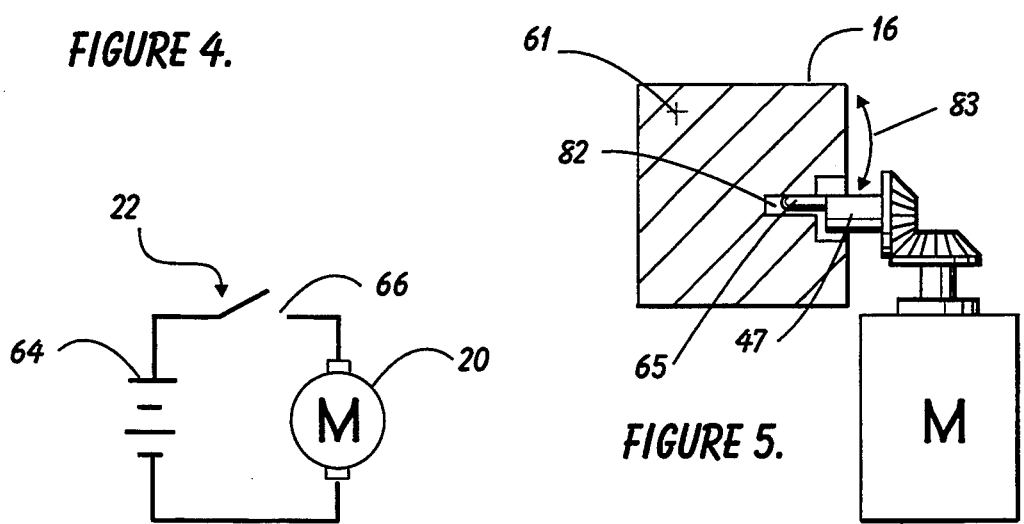
FIGURE 5.
FIGURE 6.
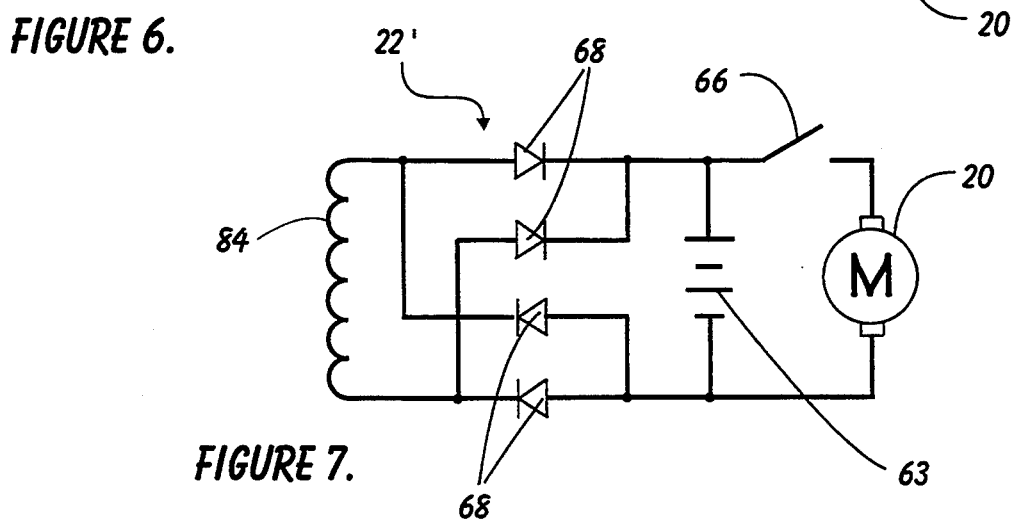
FIGURE 7.

METHOD FOR ADVANCING A GUIDE WIRE

RELATED APPLICATION

This is a continuation-in-part application based upon application Ser. No. 08/120,473, filed Sep. 13, 1993, now abandoned, which was a continuation application based upon application Ser. No. 944,473, filed Sep. 14, 1992, now U.S. Pat. No. 5,243,997.

TECHNICAL FIELD

The present invention relates generally to angioplasty and atherectomy procedures for opening a stenotic segment of a blood vessel. The present invention is particularly, though not exclusively, useful for moving a guide wire through a stenosis so that an inflatable device or a cutter device can be positioned at the stenosis.

BACKGROUND OF THE INVENTION

Blockage of human arteries is a widespread malady and, as such, represents a significant health concern. Blockages reducing blood flow through the coronary arteries to the heart can cause heart attacks, while blockages reducing blood flow through the arteries to the brain can cause strokes. Similarly, arterial blockages reducing blood flow through arteries to other parts of the body can produce grave consequences in an affected organ or limb.

The build-up of atherosclerotic plaque is a chief cause of arterial blockages reducing arterial blood flow. Consequently, several methods have been introduced to alleviate the effects of plaque build-up restricting the arterial lumen. One such method is a procedure termed angioplasty, which uses an inflatable device positioned in the artery to dilate the lumen at the stenosis. A typical angioplasty device is disclosed in U.S. Pat. No. 4,896,669 to Bhate et al. The angioplasty device of Bhate et al includes an inflatable balloon which is attached to the distal end of a hollow catheter. The proximal end of the catheter is attached to a fluid source, providing fluid communication between the balloon and the fluid source.

To treat an arterial stenosis, a guide wire is first advanced through the artery past the stenosis. Then, a balloon such as the Bhate et al balloon is introduced into the artery in a deflated state and guided through the artery over the guide wire to a position adjacent the stenosis. Fluid from the fluid source is then infused into the balloon via the catheter to inflate the balloon. As the balloon expands, it dilates the lumen of the artery. The balloon is then deflated and removed from the artery.

While effective for dilating the lumen at the stenosis, angioplasty devices, such as the Bhate et al device, do not remove the plaque from the artery. Consequently, the residual plaque either remains in place at the point of the stenosis or breaks off and migrates to other locations in the blood stream. In either case the plaque remains a continuing threat to create blockages in the circulatory system. To address the shortcomings of angioplasty, a procedure termed atherectomy has been devised which cuts and removes the plaque comprising the stenosis from the blood vessel.

An atherectomy procedure typically includes inserting a guide wire into the affected artery and advancing a hollow cutting device over the wire until the cutting device is positioned adjacent the stenosis. The cutting device is then advanced into the stenosis to cut a channel through the plaque, thereby increasing blood flow through the artery. The resulting plaque fragments are removed from the blood stream by drawing them into the hollow cutting device.

A number of atherectomy devices capable of performing this procedure are known in the art. U.S. Pat. No. 4,895,166 to Farr et al, which is assigned to the same assignee as the present invention, discloses an atherectomy device having a frustum-shaped cutter which is attached to the distal end of a hollow catheter. The cutter has two openings that define two straight, even cutting blades. The cutter is directed through the artery over a guide wire, and it is rotated as it advances into the stenosis, thereby cutting the plaque. Excised plaque enters the openings of the cutter and is subsequently removed through the hollow catheter.

A particular problem associated with angioplasty and atherectomy procedures is in moving the guide wire through the stenosis so that an inflatable balloon or cutting device can be positioned within or adjacent to the stenosis. A stenotic segment of a blood vessel presents a narrowed and often tortuous path through which the guide wire must be advanced. In some cases the stenotic segment of the blood vessel may be almost completely blocked (i.e. occluded) with atherosclerotic plaque. If the distal end of the guide wire contacts the stenosis at a location where there is no opening, the guide wire distal end must be moved laterally to find an opening, or an opening must be created. Some currently known systems oscillate or vibrate the guide wire longitudinally to cause the distal end of the wire to create an opening with a kind of picking action. The success of this maneuver depends upon the wire being stiff enough to penetrate the stenotic material. The longitudinal oscillations are not very efficient at moving the distal end of the guide wire laterally to seek out an existing opening.

In addition, as the guide wire passes through the blood vessels, it must pass through numerous turns and curves. At each turn, or even at a slight curve, the guide wire lies in direct contact, over an appreciable extent of its length, with the blood vessel wall. Indeed, the guide wire is in direct contact with the blood vessel wall over a significant part of its inserted length, and the force of contact with the wall is increased at turns and curves. This contact also occurs between the side of the wire and the stenotic material as the distal portion of the wire passes through the stenosis. Once the wire begins passing through the blood vessel, contacting the wall at a given location, it tends to remain in continual contact with the wall at that location, during most of the period of time while wire insertion is being accomplished. Therefore, as the physician advances the guide wire through the blood vessel, it drags on the vessel walls, over much of its inserted length, and this drag is experienced essentially continually during the wire insertion procedure. This means that every minute increment of advancement attempted by the physician is resisted by frictional drag over much of the length of inserted wire. This drag, resulting from friction between the wire and the wall or between the wire and the stenosis, is a significant contributor to the difficulty in advancing take guide wire through the blood vessel, and ultimately through the stenosis.

Systems which attempt to assist in advancing the guide wire by vibrating or oscillating the wire longitudinally do not alleviate the frictional drag problem, because the longitudinal vibrations or oscillations of the wire do not reduce the physical extent of contact between the wire and the wall, and they do not reduce the time of contact between the wire and the wall. At best, the longitudinal vibrations create a continual sliding contact between the wire and the vessel wall. Accordingly, the present invention recognizes the need, in the treatment of an occluded or narrowed blood vessel, for a method of lessening the frictional drag on the blood vessel wall to assist in moving a guide wire easily through the blood vessel. The present invention also recognizes the possibility of reducing this frictional drag by reducing the physical extent of contact between the guide wire and the vessel wall, and by reducing the time of contact between the wire and the wall. Both the physical extent of contact and the time of contact are reduced by introducing whip like transverse vibrations into the guide wire.

It is therefore an object of the present invention to provide a method for advancing a guide wire by transversely vibrating the guide wire such that the guide wire can be more easily moved through a blood vessel and through a stenotic segment of a blood vessel. It is another object of the present invention to provide a method that is especially adapted for use in angioplasty and atherectomy medical procedures. It is a further object of the present invention to provide a method for advancing a guide wire that is relatively easy and cost effective to perform.

SUMMARY OF THE INVENTION

In accordance with the present invention, a novel method is provided for use with a guide wire for angioplasty and atherectomy procedures. The method, simply stated, begins with introduction of the guide wire into the blood vessel by well known surgical techniques, followed by advancement through the blood vessel to the stenotic segment. During advancement, a vibrating device can be used to hold and vibrate the guide wire with a whip-like action to create a sinusoidal wave in the wire, so that it may be more easily pushed through the blood vessel and through the stenotic segment. The sinusoidal wave can be a traveling wave or a standing wave, depending upon the flexural modulus of the guide wire, the frequency of the vibration, and the damping effect of the catheter and blood vessel through which the guide wire passes, as well as the damping effect of the fluid in the vessel.

The vibrating device should be adapted to be hand held by the physician or other medical personnel during the medical procedure. It should consist of an oscillatory motion source attached to a clamp. The clamp is constrained to vibrate or oscillate with a pivoting action, causing the clamp to pivot about an axis which is substantially perpendicular to the longitudinal axis of the wire. The source of the oscillatory pivoting motion should be capable of being selectively energized for intermittent operation as required. In use, the guide wire can be releasably placed within the clamp and repositioned or advanced through the clamp as the guide wire is vibrated and pushed through the stenosis.

The novel features of the method of this invention will be best understood from the accompanying drawings, taken in conjunction with the accompanying description, in which similar reference characters refer to similar parts.

BRIEF DESCRIPTION OF THE DRAWINGS

FIG. 4 is an enlarged schematic cross sectional view of a stenotic segment of a blood vessel showing a vibrating guide wire being pushed through a stenotic segment of a blood vessel;

FIG. 5 is a schematic view of a vibrating motor and a portion of a clamp member of the vibrating device of FIG. 1, showing mechanical coupling of the clamp and motor;

FIG. 6 is an electrical schematic of a control circuit for the vibrating device; and FIG. 7 is an electrical schematic of an alternate embodiment control circuit for a vibrating device having rechargeable batteries;

DETAILED DESCRIPTION

Figure 1:
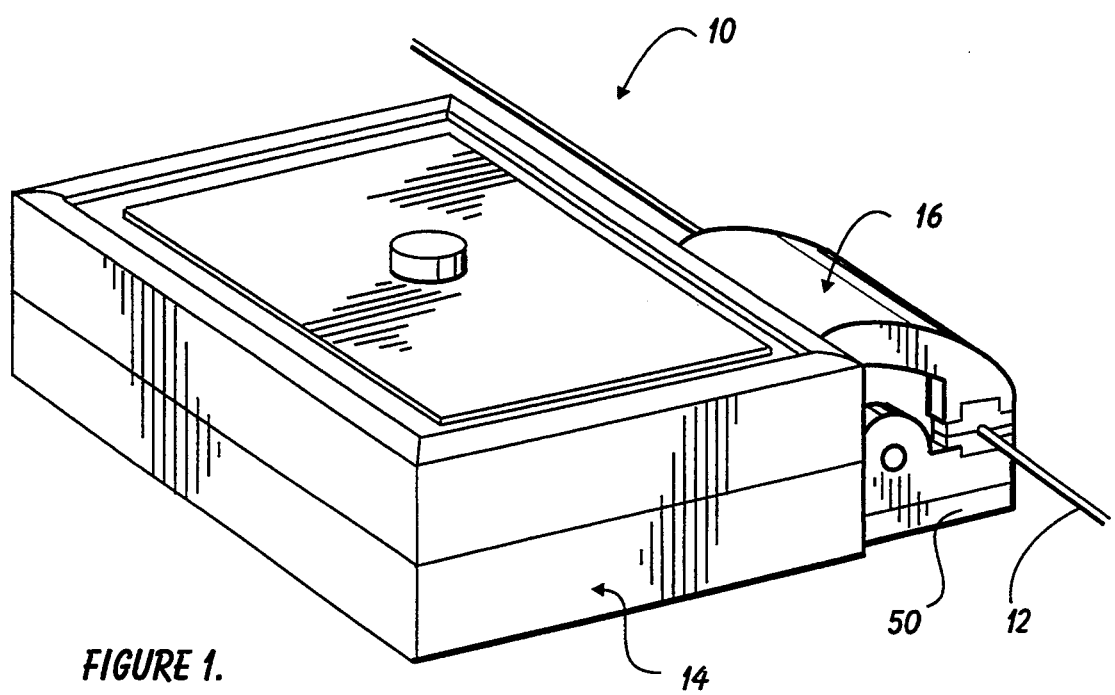
FIG. 1 is a perspective view of an exemplary vibrating device for use in performing the method of the present invention.
Figure 2:
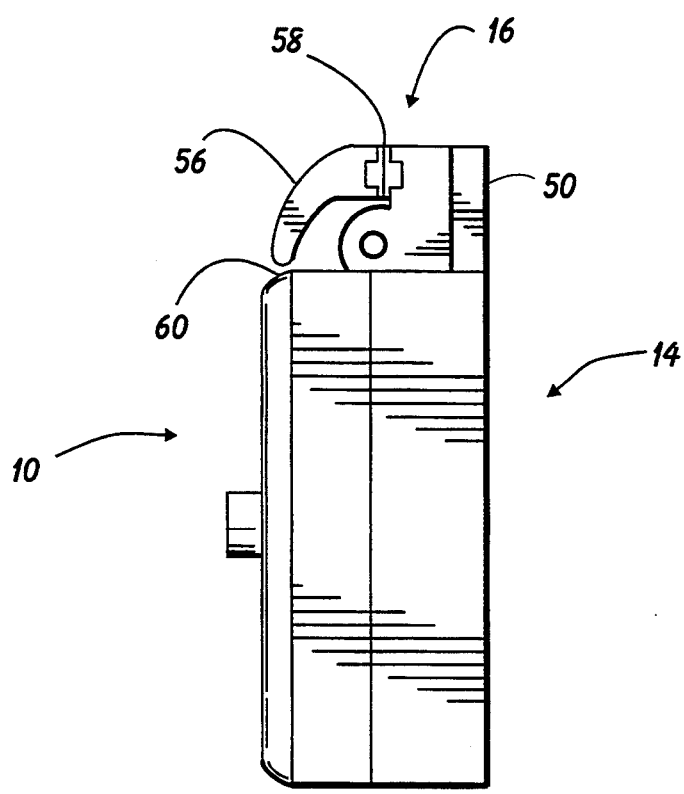
FIG. 2 is a side elevation view of the vibrating device shown in FIG. 1.

Referring to FIGS. 1 and 2, one type of vibrating device for use in performing the method of the present invention is shown and generally designated as 10. The device shown here is only an example of one way of achieving the type of whip like vibration of the guide wire that is useful in performing the method of the present invention. Other devices could also be developed to introduce this type of vibration. Further, even though the illustrated device 10 is electrically powered, other types of power, such as compressed gas, could be used as prime movers to operate the device. The vibrating device 10 is adapted to hold and vibrate an elongated flexible guide wire 12 which can be used in a medical procedure such as an angioplasty or atherectomy procedure as previously described, in which the guide wire 12 is pushed through a stenotic segment of a blood vessel. Use of the vibrating device 10, is not restricted to a solid guide wire 12, however, as it may be utilized to move other medical devices, such as a hollow wire or an elongated flexible catheter, through a blood vessel.

Figure 3:
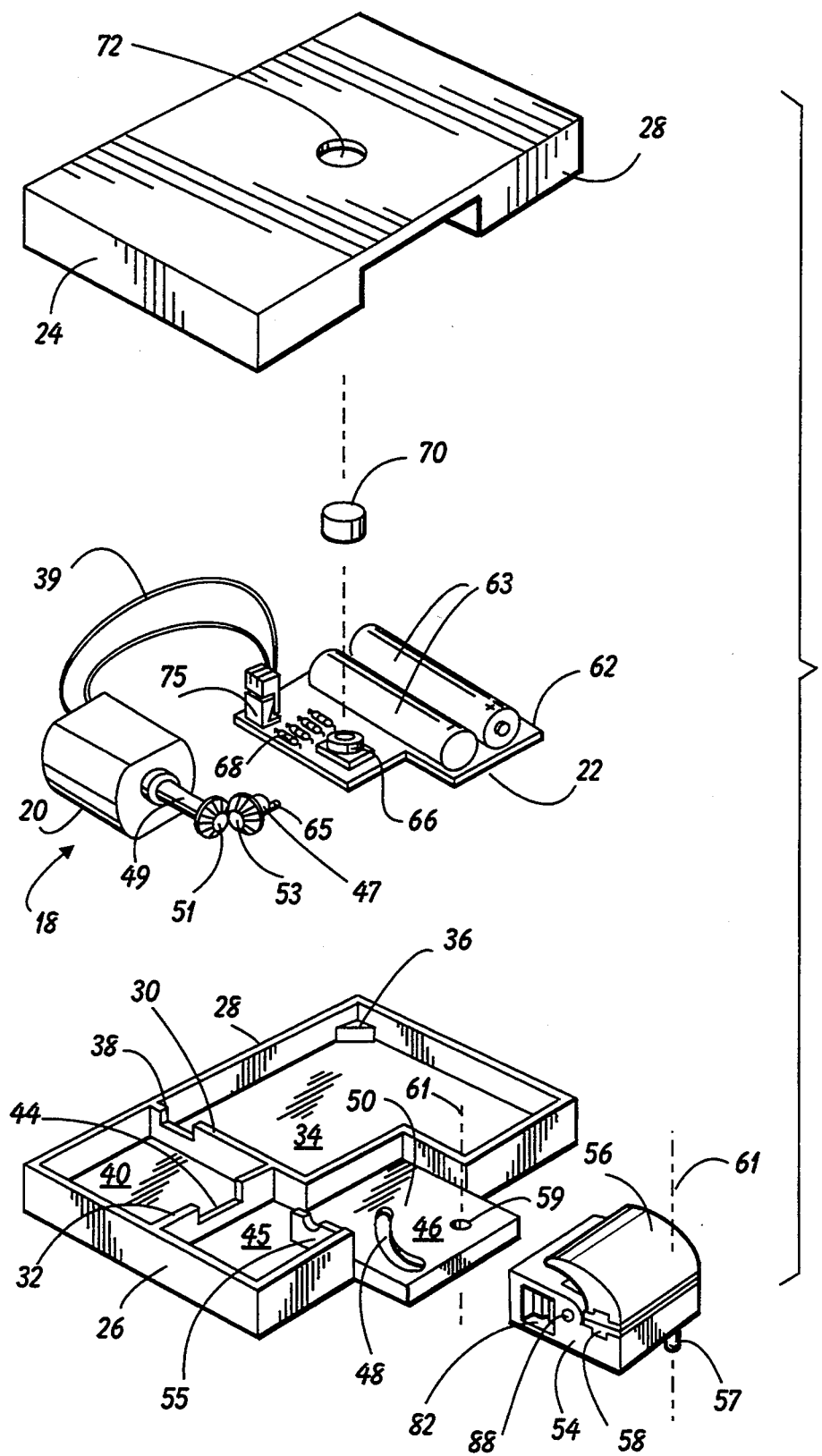
FIG. 3 is an exploded perspective view of the vibrating device shown in FIG. 1 showing the assembly of the device.

Also referring to FIG. 3, the vibrating device 10 includes a case 14, holding means in the form of a clamp member 16 pivotally mounted to the case 14 for releasably holding the guide wire 12, and vibrating means 18 in the form of a motor 20 and control circuit 22 for vibrating the clamp 16 and the guide wire 12 positioned within the clamp 16.

The case 14 is adapted to be hand held by the physician while the guide wire 12 is pushed through the blood vessel. The case 14 is sized and shaped to fit easily in a person's hand while the guide wire 12 and clamp 16 are manipulated. The case 14 has a generally rectangular outer peripheral configuration and as shown in FIG. 3 is formed in two mating halves. The case 14 may be formed of a sturdy, cleanable, material such as molded plastic.

With reference to FIG. 3, the case 14 includes a top portion 24 and a mating bottom portion 26. The top portion 24 and bottom portion 25 of the case 14 are formed substantially in a mirror image of one another. This construction includes a peripheral edge 28 that extends generally perpendicular from a top or bottom surface of the case 14, and a pair of internal ribs 30, 32. With the top portion 24 of the case assembled to the bottom portion 26, the placement of the internal ribs 30, 32 forms three separate compartments within the interior of the closed case 14.

A first compartment 34 formed within the closed case 14 houses a printed circuit board 62 with the control circuit 22 for the motor 20. The control circuit compartment 34 corresponds to the outer peripheral shape of the printed circuit board 62 for the control circuit 22. Triangular shaped standoffs 36 are formed in each corner of the control circuit compartment 34 for mounting the printed circuit board 62 within the control circuit compartment 34. A recess 38 is formed in the internal rib 30 (top and bottom) which forms one side of the control circuit compartment 34. With the top portion 24 and bottom portion 26 of the case 14 assembled, the recess 38 in the internal rib 30 forms an opening for electrical wiring 39 from the circuit board 62 to the motor 20.

A second compartment 40 formed within the closed case 14 houses the motor 20. The motor compartment 40 is generally rectangular in shape and corresponds to the outer peripheral shape of the motor 20. A recess 44 is formed in the internal rib 32 (top and bottom) which forms one side of the motor compartment 40. With the top portion 24 and bottom portion 26 of the case 14 assembled, the recess 44 in the internal rib 32 forms an opening for an output shaft 49 of the motor 20. The output shaft 49 turns a first bevel gear 51 which meshes with a second bevel gear 53. The second bevel gear 53 turns a drive shaft 47 which contacts and imparts vibratory motion to the clamp 16, as will be discussed later. This imparts a vibratory pivoting motion to a guide wire 12 secured to the clamp 16.

A third compartment 45 formed within the closed case 14 houses the first and second bevel gears 51, 53, and a bracket 55 which holds the drive shaft 47 in place. A fourth compartment 46 partially houses the clamp 16 for the guide wire 12. The clamp compartment 46 is generally rectangular in shape and substantially corresponds in shape to the outer peripheral shape of the clamp 16, leaving room for the clamp 16 to pivot as it vibrates. The clamp 16 is pivotally mounted within the clamp compartment 46 for rapid pivotal oscillatory or vibratory motion.

A pivot pin 57 projects downwardly from the bottom of the clamp 16, establishing a pivot axis 61 for the clamp 16. The pivot pin 57 fits into a pivot hole 59 in the bottom 50 of the clamp compartment 46. The pivot hole 59, therefore, also establishes the pivot axis 61. A portion of the bottom 50 of the clamp compartment 46 projects outwardly from the housing 14, so that the pivot axis 61 can be aligned substantially perpendicular to the guide wire 12. A curved guide channel 48 is located within the clamp compartment 46 for guiding or constraining the clamp 16 to move pivotably in this guide channel 48. The center of curvature of the guide channel 48 is on the pivot axis 61 of the pivot hole 59. The clamp compartment 46 is dimensioned to be slightly larger than the clamp 16 such that the clamp 16 has a range of pivotal motion within the clamp compartment 46. In addition, as before, recesses are formed in the peripheral edge 28 of the top portion 24 and bottom portion 26 of the case 14 such that in the assembled or closed case 14 an opening is formed for the clamp 16.

Figure 9:
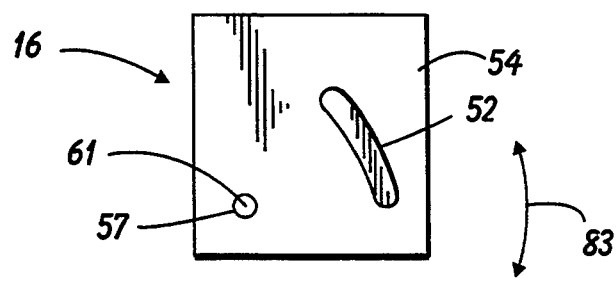
FIG. 9 is a bottom plan view of the clamp.

The clamp 16 is mounted within the clamp compartment 46 of the case 14 and is coupled to the drive shaft 47. The drive shaft 47 has an eccentric extension 65 extending from an edge of the drive shaft 47, parallel to the longitudinal axis of the drive shaft 47. As seen in FIG. 9, the bottom of the clam 16 has a curved guide rib 52 extending therefrom, with the guide rib 52 being shaped to fit into the guide channel 48 in the clamp compartment 46. The guide rib 52 has a center of curvature on the pivot axis 61 of the pivot pin 57, and a radius of curvature identical to that of the guide channel 48. The guide rib 52 has a length slightly less than the length of the guide channel 48. The clamp 16 is thus free to pivot first in one direction, and then in the other direction, along the curved path defined by the guide channel 48.

In operation of the vibrating device 10, the clamp 16 is driven to oscillate along the guide channel 48 by the motor 20. This provides the pivotal vibratory motion which then is imparted to the guide wire 12 as a whipping action. The pivotal vibratory motion of the clamp 16 is confined to a single plane parallel to the plane of the bottom surface of the clamp compartment 46, as the clamp 16 is free to move in only a single plane and cannot move in a plane perpendicular to the bottom surface of the clamp compartment 46. The dimensioning of the clamp compartment 46 prevents this perpendicular movement of the clamp 16. The whipping action of the guide wire 12 can be in the same plane as the vibratory motion of the clamp 16, but farther down the guide wire 12, the whipping motion can occur in any plane or in a constantly changing plane, at any given point.

FIG. 5 illustrates the mechanical coupling of the clamp 16 to the motor 20. The clamp 16 is formed with a stepped or counterbored slot 82 that is configured to mate with the drive shaft 47 and the eccentric extension 65. The length of the counterbored slot 82 is greater than the diameter of the drive shaft 47. The width of the central portion of the counterbored slot 82 is substantially the same as the diameter of the eccentric extension 65. The width of the counterbored portion of the slot 82 is greater than a distance which is twice the diameter of the drive shaft 47, less the width of the central portion of the slot 82. This provides lateral room for the drive shaft 47 as the clamp 16 oscillates. Rotational motion of the eccentric extension 65 translates into pivotal vibratory movement of the clamp 16 about the pivot axis 61, as indicated by the double headed arrow 83 in FIG. 5.

Figure 8:
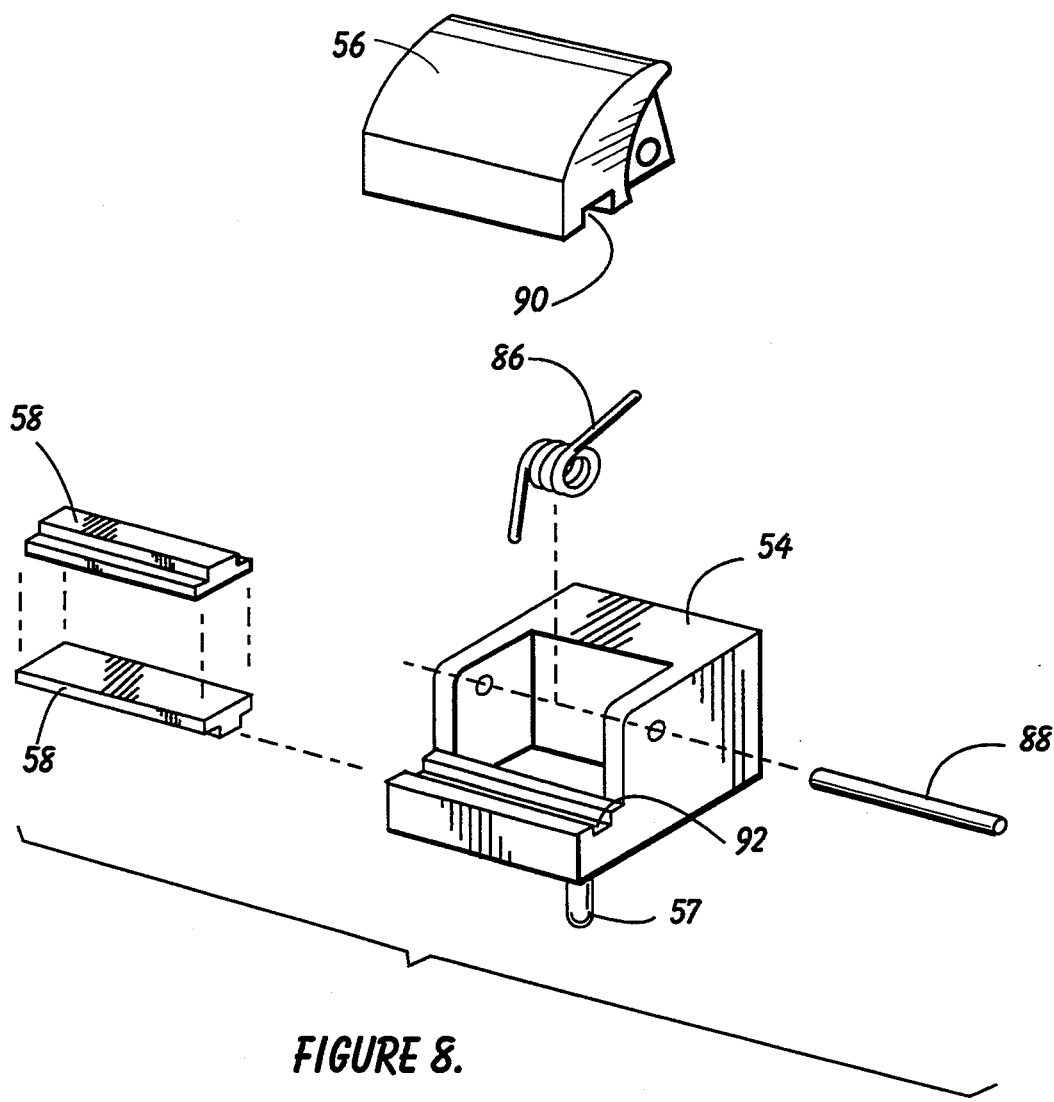
FIG. 8 is an exploded perspective view of the clamp member of the vibrating device.

Referring now to FIGS. 3 and 8, the clamp 16 includes a stationary lower jaw 54 and a moveable upper jaw 56 for releasably holding the guide wire 12. The upper jaw 56 is hingedly mounted to the lower jaw 54 on a hinge pin 88. A spring member 86 biases the upper jaw 56 in a closed direction against the lower jaw 54 of the clamp 16. Resilient contact members 58 of a material such as urethane or rubber are mounted in slots 90 and 92 formed in the upper jaw 56 and the lower jaw 54 of the clamp 16, respectively. The contact members 58 must be of sufficient stiffness to impart the desired frequency of vibration to the guide wire 12.

With this arrangement, the guide wire 12 can be pinched or held between the upper jaw 56 and the lower jaw 54, by contact with the resilient contact members 58. As shown in FIG. 2, the clamp 16 extends from a sidewall 60 of the case 14 and is positioned such that the upper jaw 56 of the clamp 16 can be manipulated by the physician while the vibrating device 10 is held in the physician's hand. A vibrating guide wire 12 can thus be continuously advanced through the blood vessel using the clamp 16 to alternately hold and release the guide wire 12.

A suitable control circuit 22 for the vibrating device 10 is shown in FIG. 6. In its simplest form the control circuit 22 includes a power source such as a battery 64, and a normally open on-off switch 66 for operating the motor 20. As an example, the battery 64 may be a AA 1.5 volt disposable alkaline battery. Two such batteries 64 may be coupled together to provide a 3 volt power source. Alternatively, as shown in FIG. 7, rechargeable batteries 63 may be used with a control circuit 22'. This recharging control circuit 22' includes diodes 68 and an inductive element 84. This latter embodiment is shown in FIG. 3. An external power lead could be used in lieu of the batteries, or compressed air or some other prime mover could be substituted.

As shown in FIG. 3, the electrical components of the control circuit 22 or 22' for the vibrating device 10 are mounted on the printed circuit board 62. An externally mounted push button 70 operates the on-off switch 66 for actuating the motor 20. An opening 72 is formed in the top portion 24 of the case 14 for accessing the pushbutton 70. The printed circuit board 62 also includes a connector 75 which connects wiring 39 from the motor 20 to components located on the printed circuit board 62.

As previously explained, the motor 20, is adapted to engage the clamp 16 and impart a pivotal vibratory motion to the clamp 16 and to a guide wire 12 held within the clamp 16. A suitable motor 20 has a small fractional horsepower output and turns at relatively high rpm's, preferably 7500 rpm or greater. If the bevel gears 51, 53 have equal numbers of teeth, this motor speed will result in a vibrational frequency of the clamp 16 of at least 125 Hz. The frequency with which the clamp 16 and the guide wire 12 will vibrate will be directly proportional to the rotational frequency of the output shaft 49 of the motor 20. Unlike the clamp member 16, which is free to vibrate in only a single plane, the guide wire 12 within the blood vessel will vibrate in three dimensions. Regardless of the plane in which the guide wire 12 vibrates at any given location, the direction of the vibration will be mostly transverse to the longitudinal axis of the guide wire 12, with a relatively small longitudinal component, resulting in a whip like action, to facilitate advancement through the blood vessel or through a stenosis.

Referring now to FIG. 4, the vibrating device 10 is shown being used in performing the method of the present invention. A blood vessel such as an artery 74 includes a stenotic segment 76 wherein a build up of atherosclerotic plaque 78 is located. In order to perform an angioplasty or atherectomy procedure a guide wire 12 must be advanced along the blood vessel and pushed through the stenotic segment 76 to locate an inflatable balloon or cutter device within the stenotic segment 76. Initially, the guide wire 12 is placed into the artery 74 utilizing an introductory catheter 80 that is percutaneously inserted into the artery 74. The guide wire 12 cart then be directed through the artery 74 to the stenotic segment 76 of the artery 74, utilizing well known techniques such as radiological tracking. The guide wire 12 may in fact be formed with a radiopaque tip 84 at its distal end to facilitate such a procedure.

A portion of the guide wire 12 can be fastened to the clamp 16 of the vibrating device 10 so that the guide wire 12 can be vibrated and pushed along the blood vessel and through the stenotic segment 76 of the artery 74. As the guide wire 12 vibrates transversely, the extent of contact between the wire 12 and the artery wall is significantly reduced, with contact only occurring at essentially the crests of the sinusoidal waves. The great preponderance of the length of the wire is between the crests at any point in time, so the extent of contact between the wire and the vessel wall is dramatically reduced. The time of contact is also significantly reduced, with each contact between the wire and the vessel wall lasting only for an instant of time. Therefore, any given point on the wire is subject to contact with the wall for only a very short time, as compared to the long time between contacts, when the given point is free from contact. Any incremental advancement of the wire during the free time between contacts is completely free from frictional drag, at the given point. These reductions of the extent of contact and the time of contact result in a significant reduction in the frictional drag as the wire is advanced through the blood vessel.

The build up of plaque 78 in the artery 74 would normally make it difficult to pass the guide wire 12 through the stenotic segment 76. By selectively actuating the motor 20 to vibrate the guide wire 12, however, the physician is more easily able to direct the guide wire 12 through the plaque 78. The end of the vibrating guide wire 12 in effect moves laterally to find an open channel through the plaque 78, or alternatively the combined longitudinal and transverse motion of the wire end cuts its own path through the plaque. This can result, at least partially, from a whipping of the distal end of the guide wire 12.

The clamp 16 of the vibrating device 10 can be used to hold the guide wire 12 while it is advanced through the blood vessel or the stenotic segment and to alternately grip and release the guide wire 12 while the proximal end of the guide wire 12 is relocated with respect to the vibrating device 10. During this procedure the vibrating device 10 is held in the physician's hand. The physician operates the push button 70 which controls the motor 20 and manipulates the guide wire 12 and clamp 16 as required.

Thus the method of the present invention provides an improved method for advancing a wire, particularly suited to angioplasty and atherectomy procedures. While the particular method for advancing a guide wire as herein shown and disclosed in detail is capable of obtaining the objects and providing the advantages hereinbefore stated, it is understood that this particular method is merely illustrative of the presently preferred practice of the invention. It is further understood that the present invention is not intended to be so limited, and that other variations of this method are further possible within the scope of the present invention.

I claim:

1. A method for advancing an elongated flexible element through a blood vessel, comprising the steps of:

inserting a leading end of a flexible element into the blood vessel;

advancing said flexible element along the blood vessel until frictional resistance develops from contact between a first plurality of points along said flexible element and a second plurality of corresponding points along the wall of said blood vessel; and overcoming said resistance by introducing sinusoidal transverse vibrations into said flexible element, thereby reducing the length of contact between said flexible element and said vessel wall, and thereby reducing the time of contact between said first plurality of points and said second plurality of corresponding points.

2. A method for advancing an elongated flexible element through a blood vessel, comprising the steps of:
   inserting a leading end of a flexible element into the blood vessel;
   advancing said flexible element along the blood vessel until resistance is met, by pushing said flexible element into the blood vessel; and
   introducing sinusoidal transverse vibrations into said flexible element to overcome said resistance, while pushing said flexible element farther into the blood vessel.

3. A method for advancing a flexible element through a blood vessel as claimed in claim 2, further comprising the step of radiographically tracking the location of said leading end of said flexible element.

4. A method for advancing a flexible element through a blood vessel as claimed in claim 2, further comprising the steps of:
   advancing said leading end of said flexible element to an obstruction in the blood vessel;
   introducing sinusoidal transverse vibrations into said flexible element to find a path through said obstruction; and
   pushing said leading end of said flexible element through said obstruction.

5. A method for advancing a flexible element through a blood vessel as claimed in claim 2, wherein said flexible element is a guide wire.

6. A method for advancing a flexible element through a blood vessel as claimed in claim 2, wherein the step of introducing vibrations into said flexible element while pushing said flexible element comprises the steps of:
   clamping a vibration means onto said flexible element at a first location;
   introducing sinusoidal transverse vibrations into said flexible element at said first location, with said vibration means;
   releasing said flexible element from said vibration means;
   clamping said vibration means onto said flexible element at a second location; and
   introducing sinusoidal transverse vibrations into said flexible element at said second location, with said vibration means.

7. A method for advancing a flexible element through a blood vessel as claimed in claim 6, wherein said sinusoidal transverse vibrations are introduced by the steps of:
   attaching an oscillatory motion source to a clamp;
   constraining said clamp to oscillate pivotally about a preferred pivot axis;
   clamping said clamp onto said flexible element; and
   energizing said oscillatory motion source to cause said clamp to oscillate pivotally about said preferred pivot axis, thereby imparting an oscillatory whip action to said flexible element.

8. A method for advancing a flexible element through a blood vessel as claimed in claim 7, wherein said clamp is clamped onto said flexible element so that said preferred pivot axis is perpendicular to the longitudinal axis of said flexible element.

9. A method for advancing a guide wire through a blood vessel, comprising the steps of:
   inserting a leading end of a guide wire into the blood vessel;
   advancing said guide wire along the blood vessel until resistance is met in the blood vessel;
   attaching a clamp at a selected point on said guide wire to define a pivot axis transverse to said guide wire; and
   pivoting said clamp about said pivot axis in an oscillating fashion, thereby introducing transverse sinusoidal vibrations into said guide wire to overcome said resistance and to assist said guide wire in advancing farther through the blood vessel.

10. A method for advancing a guide wire through a blood vessel, comprising the steps of:
    attaching an oscillatory motion source to a clamp;
    constraining said clamp to oscillate pivotally about a preferred pivot axis;
    inserting a leading end of said guide wire into the blood vessel;
    advancing said guide wire along the blood vessel until resistance is met in the blood vessel, by pushing a first length of said guide wire into the blood vessel;
    clamping said clamp onto said guide wire, with said preferred pivot axis of said clamp being substantially perpendicular to the longitudinal axis of said guide wire;
    energizing said oscillatory motion source to cause said clamp and said guide wire to oscillate about said pivot axis, thereby introducing transverse vibrations into said guide wire to create a sinusoidal waveform in said guide wire, while pushing a second length of said guide wire into the blood vessel, until said resistance is overcome.

11. A method for advancing a guide wire through a blood vessel as claimed in claim 10, further comprising the step of radiographically tracking the location of said leading end of said guide wire.

12. A method for advancing a guide wire through a blood vessel as claimed in claim 10, wherein the step of introducing transverse vibrations into said guide wire while pushing said guide wire comprises the steps of:
    clamping said clamp onto said guide wire at a first location;
    introducing transverse vibrations into said guide wire at said first location, by energizing said oscillatory motion source;
    releasing said guide wire from said clamp;
    clamping said clamp onto said guide wire at a second location; and
    introducing transverse vibrations into said guide wire at said second location, by energizing said oscillatory motion source.

* * * * *